(12) United States Patent
Eerden

(10) Patent No.: US 8,560,065 B2
(45) Date of Patent: Oct. 15, 2013

(54) CPR MONITORING AND REPORTING SYSTEM AND METHOD

(75) Inventor: Jacco Eerden, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 377 days.

(21) Appl. No.: 12/678,678

(22) PCT Filed: Sep. 12, 2008

(86) PCT No.: PCT/IB2008/053692
§ 371 (c)(1),
(2), (4) Date: Mar. 17, 2010

(87) PCT Pub. No.: WO2009/037621
PCT Pub. Date: Mar. 26, 2009

(65) Prior Publication Data
US 2010/0211127 A1    Aug. 19, 2010

Related U.S. Application Data

(60) Provisional application No. 60/974,113, filed on Sep. 21, 2007.

(51) Int. Cl.
*A61N 1/39* (2006.01)

(52) U.S. Cl.
USPC .................................................. 607/5

(58) Field of Classification Search
USPC .................................... 607/3, 5, 6
See application file for complete search history.

(56) References Cited

U.S. PATENT DOCUMENTS

| | | | | |
|---|---|---|---|---|
| 5,348,020 A | * | 9/1994 | Hutson | 600/509 |
| 6,292,692 B1 | * | 9/2001 | Skelton et al. | 607/5 |
| 7,610,095 B2 | * | 10/2009 | Naisberg | 607/45 |
| 7,650,181 B2 | * | 1/2010 | Freeman et al. | 600/510 |
| 2006/0025698 A1 | * | 2/2006 | Nakagawa et al. | 600/513 |
| 2007/0060785 A1 | | 3/2007 | Freeman et al. | |
| 2009/0240295 A1 | * | 9/2009 | Kellum | 607/5 |

FOREIGN PATENT DOCUMENTS

| | | |
|---|---|---|
| EP | 0623334 A | 11/1994 |
| EP | 1938779 A | 7/2008 |
| WO | 2007081609 A | 7/2007 |

* cited by examiner

*Primary Examiner* — Scott Getzow
*Assistant Examiner* — Amanda Patton

(57) ABSTRACT

A system for providing improved feedback on administration of CPR is disclosed. A compression sensor (14) is incorporated into a pad (12) adapted to be positioned between a rescuer's hands and a victim's chest. The compression sensor provides an output to a feedback control module (16) that records the output and segments the output into individual compression cycles that are analyzed with respect to evaluation criteria, such as those related to guidelines for effective CPR. The results of the analysis are formatted into a matrix having elements that represent the results of the analysis for an individual compression cycle with respect to an evaluation criterion. An example of the matrix elements is a graph plotting a property of compressions within one of the individual compression cycles over time. Portions of the graphs failing to satisfy one of the evaluation criteria may be highlighted.

19 Claims, 4 Drawing Sheets

CPR MONITORING AND REPORTING SYSTEM AND METHOD

This invention relates generally to cardio-pulmonary resuscitation (CPR) feedback systems, and more particularly, to CPR feedback systems that provide feedback for overall CPR effectiveness.

Sudden cardiac arrest (SCA) is one of the largest causes of death in the United States. SCA most often occurs without warning, striking people with no previously recognized symptoms of heart disease. It is estimated that more than 1000 people per day are victims of sudden cardiac arrest in the United States alone. SCA results when the electrical component of the heart no longer functions properly causing an abnormal sinus rhythm.

The chances of surviving a cardiac arrest decrease with time after the attack. Quick response to an arrest by performing CPR and/or by administering a defibrillating shock is therefore of critical importance. The American Heart Association's "Chain of Survival" recites the following steps:

1. Rapid access to medical care, such as by activating an emergency response system (e.g., by calling an ambulance);
2. Rapid CPR initiated by a bystander or other early caregiver to help the victim survive until more advanced care arrives;
3. Rapid defibrillation; and
4. Rapid application of Advanced Cardiac Life Support (ACLS), such as airway management, drugs, etc. The benefits of this approach are discussed in more detail in Cummins, et al., "Improving Survival From Sudden Cardiac Arrest: The 'Chain of Survival Concept," 83 *Circulation* 18332-47 (May 1991).

In is important for CPR to be performed correctly in order to increase the victim's likelihood of survival. In particular, chest compressions are often not performed properly by many lay rescuers and trained rescuers. Guidelines issued by the American Heart Association, "2005 American Heart Association Guidelines for Cardiopulmonary Resuscitation and Emergency Cardiovascular Care," Circulation Vol. 112, Issue 24 (December 2005), have recently emphasized the importance of providing an adequate number of chest compressions, compressing the chest to an adequate depth, allowing the chest to recoil after each compression, and minimizing interruptions in chest compressions.

Current CPR feedback and recording systems provide feedback during the CPR performance for both training and real rescues. However, it is difficult to monitor performance during CPR training or actual resuscitation sessions and to judge how well the user adapted and/or used the feedback.

Accordingly, it would be an advancement in the art to provide an improved system and method for providing feedback on the administration of CPR.

In one aspect of the invention, a compression sensor is incorporated into a pad adapted to be positioned between a rescuer's hands and a victim's chest during administration of CPR. The compression sensor provides an output signal to a feedback control module that records the output signals and segments the output into individual compression cycles. The output signal is also analyzed to compare the individual compression cycles to evaluation criteria that may include minimum and maximum values for peak compression, a maximum compression depth for release, a minimum and a maximum frequency, and a maximum inactivity interval. The results of the analysis are formatted into a matrix, the elements of which each correspond to the results of the analysis of an individual compression cycle with respect to a test criteria.

In another aspect of the invention, the matrix elements each include a graph plotting a property of compressions within at least one of the individual compression cycles over time. The graphs may include highlighted portions highlighted according to a pattern, the highlighted portions corresponding to portions of the graphs failing to satisfy one of the evaluation criteria.

Figure 1:
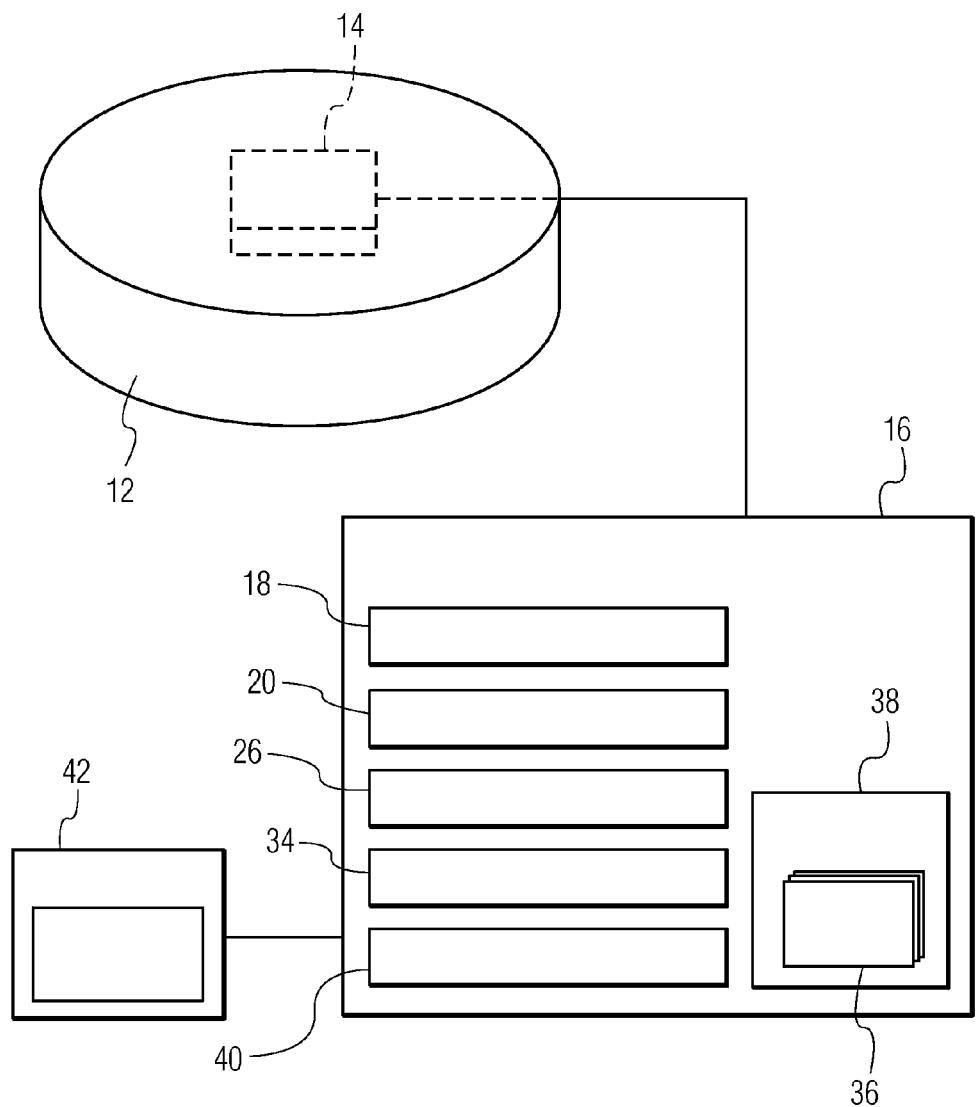
FIG. 1 is a schematic block diagram of a feedback controller in accordance with an embodiment of the present invention.

Referring to FIG. 1, a CPR feedback system 10 includes a pad 12 for positioning on a victim's chest. The rescuer presses against the pad 12 when performing chest compressions. The pad 12 incorporates a sensor 14 for sensing compressions. The sensor 14 may be a pressure sensor, motion sensor, accelerometer, or like device suitable for producing an output signal corresponding to the force and/or motion experienced by the pad 12 during CPR compressions.

The output of the sensor 14 is provided to a feedback control module 16. The output of the sensor may be processed by a signal conditioner 18 that performs such functions as removing noise, converting the output to a digital signal, and other signal processing functions known in the art for removing artifacts from a transducer signal and preparing the signal for processing.

The output of the signal conditioner 18 is provided to a segmentation module 20. The segmentation module 20 records the output of the signal conditioner 18 over a time interval during a CPR session. The segmentation module 20 then analyzes the recorded data to divide the recorded data into portions corresponding to individual compression cycles within the CPR session. CPR typically includes a number of cycles each including performing a specified number of compressions followed by ventilations. Accordingly, the segmentation module 20 may identify segments of data corresponding to the series of chest compressions of each cycle. The segmentation module 20 may identify the segments by identifying series of compressions bounded by intervals of inactivity corresponding to the ventilation stage of each cycle in which no compressions are performed.

Figure 2:
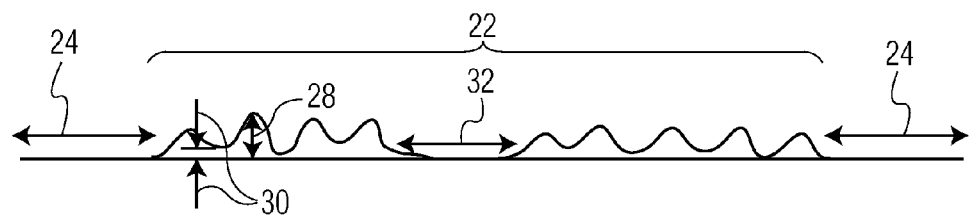
FIG. 2 is a graph illustrating compressions performed during a CPR compression cycle.

Referring to FIG. 2 while still referring to FIG. 1, a plot of data recorded by the segmentation module 20 may include various peaks corresponding to individual compressions. The segments 22 identified by the segmentation module 20 include groups of peaks corresponding to the compression stage of a cycle may be separated from one another by intervals 24 of inactivity during which ventilations are performed. The segments 22 may be analyzed by an extraction module 26 that compiles data describing some or all of the compressions within a segment 22. The data extracted may include the peak compression depth 28 of some or all of the compressions, the minimum compression 30 between some or all of the peaks, and the location and/or duration of intervals 32 of inactivity between peaks. The interval 32 represents inactivity during a compression cycle unrelated to ventilation. The extraction module 26 may also determine a frequency of the compressions. The frequency may be calculated for the entire segment 22 or be calculated for smaller sub-segments, or smaller sub-segments centered at each individual peak within the segment 22.

The data extracted by the extraction module 26 is then processed by an evaluation module 34 that compares the extracted data to criteria 36. The criteria 36 may include, for example, minimum and maximum values for peak compression, a maximum compression depth for release, a minimum and a maximum frequency, and a maximum inactivity interval. The criteria 36 may be stored in a memory 38 coupled to or incorporated in the feedback control module 16. The memory 38 may be a read/writeable memory such that the criteria 36 may be changed according to the most current knowledge and practices.

The results of the evaluation performed by the evaluation module 34 are processed by an output module 40 to generate an output for a display 42, a printer, or other output device. The output module 40 formats and presents the evaluation in a human readable form. The results of the evaluation may also be stored in the memory 38 for later review and evaluation, either on the display 42 or another device. For example, the memory 38 may be a removable storage device such as flashcard media by which the evaluation results can be ported to another computerized system. The evaluation results can also be ported by wire or wirelessly to another device, if desired.

Figure 3:
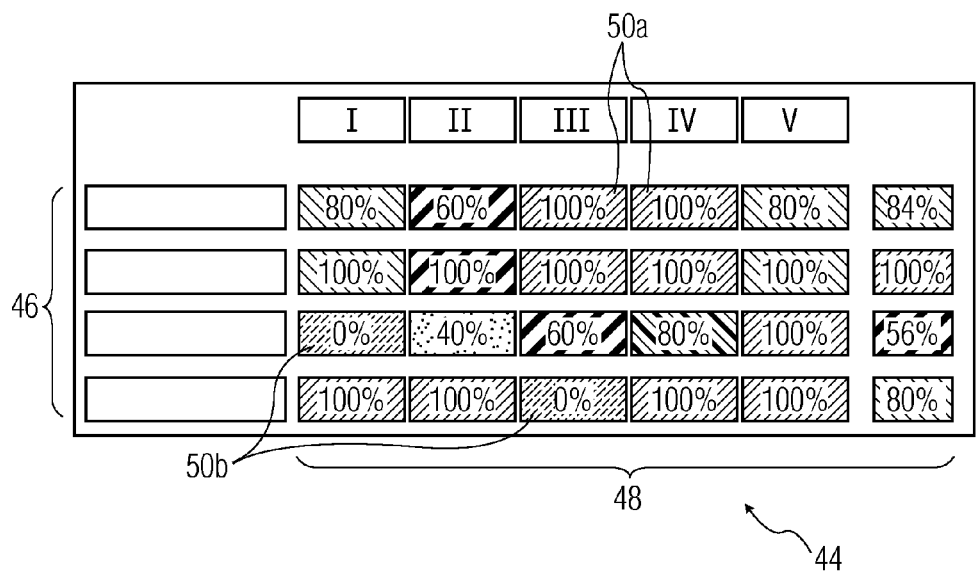
FIG. 3 is an illustration of an output display from a feedback controller in accordance with an embodiment of the present invention.

Referring to FIG. 3, the evaluation may be formatted as a display matrix 44 having rows (or columns) 46 corresponding to the evaluation criteria and columns (or rows) 48 corresponding to individual compression cycles. The individual compression cycles are indicated in FIG. 3 by Roman numerals I-V across the top of the matrix 44. The elements 50 of the matrix 44 correspond to the evaluation of an individual compression cycle with respect to one of the evaluation criteria. For example, matrix 44 includes elements for compression release ("Release"), compression depth ("Depth"), compression frequency or rate ("Rate"), and inactivity ("Inactivity") during a compression cycle. In some embodiments, the output module 40 provides the matrix 44 to a Web-based application, personal digital assistant (PDA), projector, printer, general purpose computer coupled to a monitor, or other display device.

In some embodiments, the elements 50 of the matrix 44 include percentage notations indicating a percentage of compressions during an individual compression cycle that satisfy the respective evaluation criteria. For example, with respect to compression depth, the elements 50 may indicate the percentage of compressions that lie between acceptable minimum and maximum compression depths. With respect to compression release, the elements 50 may indicate the percentage of compressions after which the rescuer allowed the victim's chest to return to sufficient release depth between a minimum and maximum release depth. Such an embodiment is illustrated in FIG. 3. In some embodiments, the elements 50 of the matrix include numbers indicating the number of compressions within an individual compression cycle that satisfy the evaluation criteria. Additionally, with respect to inactivity during an individual compression cycle, the elements 50 may indicate by using one or more colors or words, that a compression cycle did or did not have periods of inactivity, as will be described in more detail below.

In some embodiments, the elements 50 may also be highlighted to indicate which of the individual compression cycles were adequate or inadequate with respect to the evaluation criteria. For example, elements 50a are coded green, inasmuch as the evaluation criteria were met for the corresponding compression cycle. Elements 50b are coded red inasmuch as the evaluation criteria were not met for the corresponding compression cycle. In some embodiments, the elements 50 are coded according to a color code including colors for a plurality of sub-ranges within a range of adequate and inadequate values.

Figure 4:
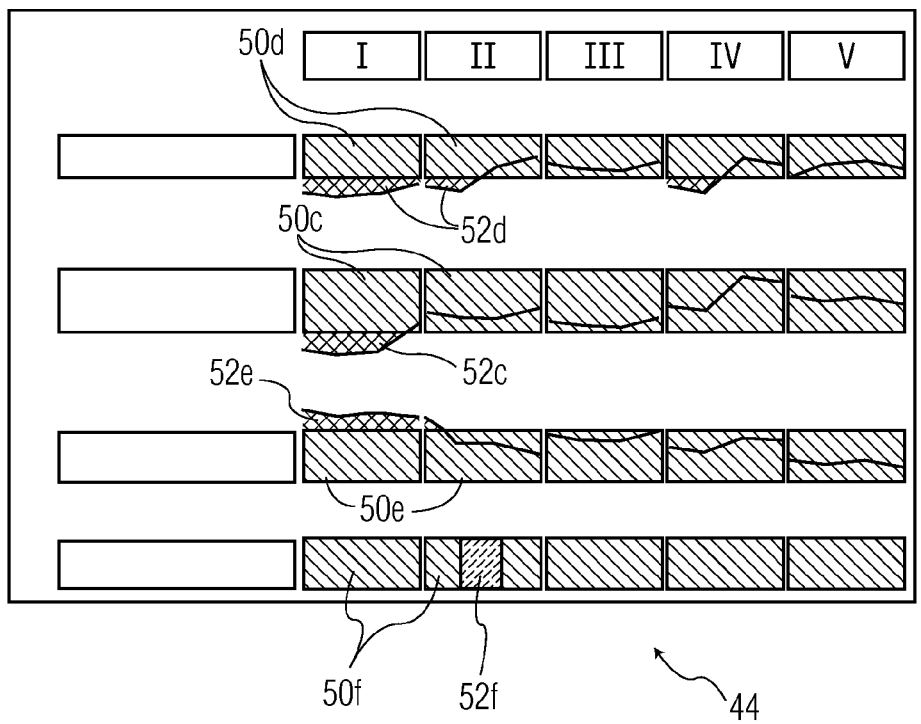
FIG. 4 is an illustration of an alternative output display from a feedback controller in accordance with an embodiment of the present invention.

Referring to FIG. 4, in some embodiments the elements 50 include graphs plotting a property of an individual compression cycle over time. Either the height (in the case of rows) or width (in the case of columns) of the elements can be used to represent the acceptable range for the respective evaluation criteria. For example, elements 50c indicate how the peak compression depth varies with each compression within an individual compression cycle. Elements 50d indicate how the minimum compression depth between compressions (the release depth) varies within each individual compression cycle. Elements 50e indicate how the frequency of compressions varied within each individual compression cycle.

The elements 50c-50e may further include highlighted portions indicating portions of the graph that fail to satisfy one of the test criteria. For example, elements 50c include a highlighted portion indicating an instance where the peak compression depth either exceeded a specified maximum compression depth or fell below a specified minimum compression depth. FIG. 4 illustrates a highlighted example 52c of where the peak compression depth exceeds the maximum compression depth. Elements 50d include highlighted portions 52d indicating where the release depth between compressions was greater than a specified release depth. Elements 50e include highlighted portions 52e indicating where the frequency of compressions either exceeded a specified maximum frequency or fell below a specified minimum frequency. The example illustrated by FIG. 4 shows a frequency of compression that exceeds the maximum accepted frequency.

Elements 50f contain a bar 52f if there are any periods of inactivity within each individual compression cycle, with the length of the bar indicating the duration of the inactivity. In some embodiments, elements 50f only contain a bar indicating the length of periods of inactivity within an individual compression cycle if it contains a period of inactivity exceeding a specified threshold duration. In some embodiments, the bar has text superimposed thereon that indicates the duration of the period of inactivity. In some embodiments, a bar is displayed only if the period of inactivity fails to satisfy an evaluation criteria. In other embodiments, periods of inactivity are shown regardless of duration and those exceeding an evaluation criteria are highlighted. In still other embodiments, only periods of inactivity exceeding a first threshold are displayed and of those, only those having a duration exceeding a second threshold corresponding to an evaluation criteria are highlighted.

Figure 5:
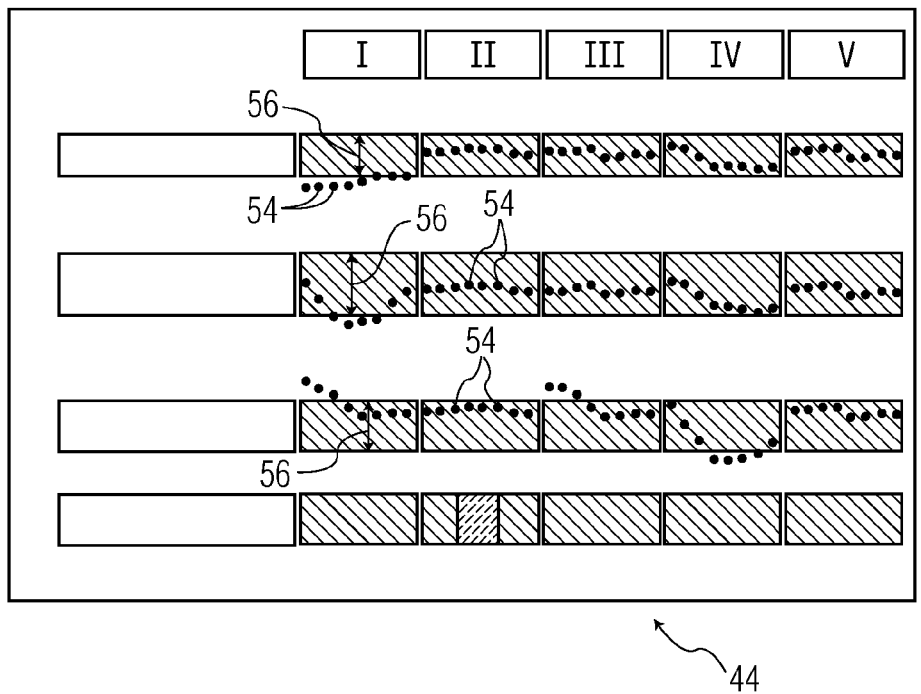
FIG. 5 is an illustration of another alternative output display from a feedback controller in accordance with an embodiment of the present invention.

Referring to FIG. 5, in an alternative embodiment, the graphs include a series of discrete data points 54, with each data point representing an average, or other combination, of multiple compressions, such as two or three, within a compression cycle. The data points 54 may be superimposed on zones 56 indicating ranges of acceptable values for each characteristic of a compression cycle.

Figure 6:
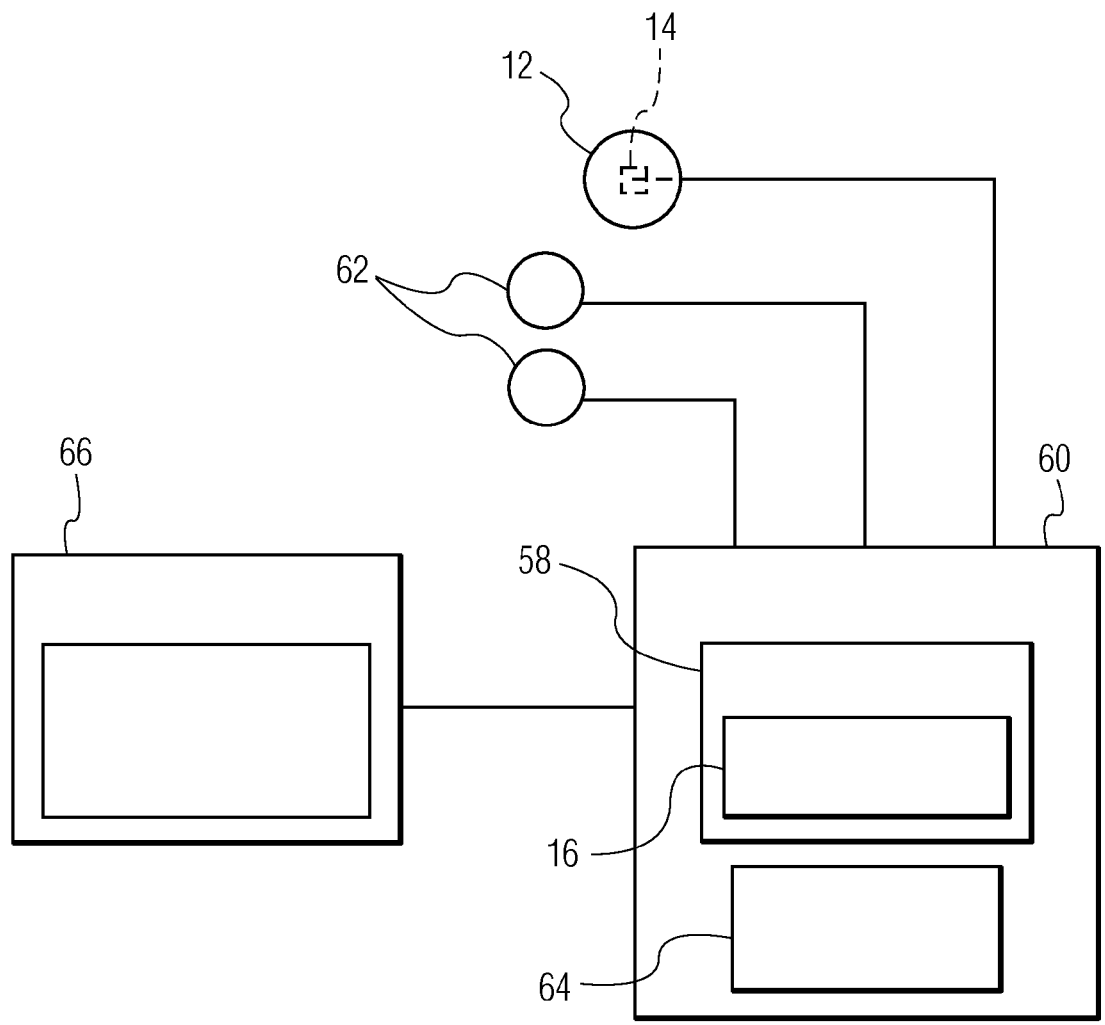
FIG. 6 is a schematic block diagram of an automatic external defibrillator (AED) incorporating a feedback controller in accordance with an embodiment of the present invention.

FIG. 6 illustrates a feedback control module 16 is incorporated into a controller 58 of an automatic external defibrillator (AED) 60. The AED in this example includes electrodes 62 for contacting a victim's skin when administering a defibrillating shock. The AED 60 further includes a power source 64 providing electrical power for delivering a defibrillating shock and for powering the electronic components of the AED. The controller 58 may be programmed to control the delivery of electrical power from the power source 64 to the electrodes 62. The controller 58 also detects the electrical activity of the victim's heart through the electrodes 62 and analyzes the electrical activity to determine whether a shock should be administered. The AED 60 further includes a display 66 and the controller is programmed to display instructions for operating the AED on the display 66. In such embodiments, the output module 40 may therefore display results of the evaluation of CPR as discussed above on the same display 66. In other embodiments, the AED 60 may include a printer for generating a printout of the results of the evaluation of CPR. Another alternative is to port the evaluation matrix to another computerized system for display.

In addition to incorporation into an AED, the feedback control module 16 may be incorporated into an AED training device or an ALS (Advanced Life Support) patient monitor/defibrillator.

The invention described herein provides an improved system and method for providing feedback on CPR. The feedback control module 16 enables a rescuer or trainee to view overall performance, rather than solely instantaneous feedback. The feedback control module 16 therefore enables rescuers and trainees to more effectively improve their technique, resulting in greater survival rates for victims. The feedback control module 16 further enables a rescuer to determine the onset of fatigue when performance begins to fall consistently outside of evaluation criteria, enabling rescuers to know when to replace one another.

The above described invention may also be used in conjunction with providing immediate feedback for training purposes. For example, a trainee may perform a CPR session on a mannequin and be provided substantially immediate feedback on compression depth, release depth, frequency, and inactivity by tones or displays as is known in the art. The trainee may then perform a CPR session without immediate feedback and following the session receive a scorecard according to the systems and methods described above. Thus, the trainee will be able to assess the extent to which the guidelines have been learned and become habitual.

From the foregoing it will be appreciated that, although specific embodiments of the invention have been described herein for purposes of illustration, various modifications may be made without deviating from the spirit and scope of the invention. Reference to modules constituting embodiments of the invention indicate structures and steps for performing the functions attributed to a module, however the structures for performing the functions attributed to a module may be operate at different times or include multiple distinct structures that may or may not be collocated. Accordingly, the invention is not limited except as by the appended claims.

What is claimed is:

1. An apparatus for providing feedback on CPR during a CPR session comprising:
    a compression sensor adapted to be positioned between a rescuer's hands and a victim's chest, the compression sensor producing a compression output;
    a feedback control module coupled to the compression sensor, the feedback control module programmed to record the compression output during the CPR session;
    analyze the recorded compression output and identify individual compression cycles;
    compare the individual compression cycles to a plurality of evaluation criteria;
    output to a display device a matrix of comparisons including matrix elements, each matrix element corresponding to a comparison of one of the individual compression cycles to one of the plurality of evaluation criteria.

2. The apparatus of claim 1, wherein one of the rows and columns of the matrix correspond to individual compression cycles and the other of the rows and columns corresponds to the plurality of evaluation criteria.

3. The apparatus of claim 1, wherein the evaluation criteria include at least one of compression depth, compression release, frequency, and inactivity.

4. The apparatus of claim 1, wherein the matrix elements include highlighted portions corresponding to portions of individual compression cycles failing to satisfy an evaluation criterion.

5. The apparatus of claim 1, wherein the matrix elements include first highlighted portions having a first color and second highlighted portions having a second color, the first highlighted portion corresponding to individual compression cycles failing to satisfy an evaluation criterion and the second highlighted portion corresponding to individual compression cycles satisfying the evaluation criterion.

6. The apparatus of claim 1, wherein each of the matrix elements include a graph plotting a property of compressions within an individual compression cycle over the time of the CPR session.

7. The apparatus of claim 6, wherein one or more of the graphs include one or more highlighted portions highlighted according to a pattern, the highlighted portions corresponding to portions of the individual compression cycles failing to satisfy one of the evaluation criteria.

8. The apparatus of claim 1, wherein the display device comprises at least one of a display screen and a printer.

9. The apparatus of claim 1, further comprising an automatic external defibrillator having a power source and electrodes for administering a defibrillating shock to the victim, the feedback control module coupled to the power source and programmed to monitor compressions applied to the compression sensor.

10. A method for providing feedback on CPR comprising:
    performing chest compressions on a victim during a CPR session through a compression sensor interposed between the victim's chest and a rescuer's hands;
    recording an output from the compression sensor during the CPR session;
    analyzing the recorded compression output to identify individual compression cycles;
    comparing each individual compression cycle to a plurality of evaluation criteria;
    outputting a matrix of comparisons including matrix elements, each matrix element corresponding to a comparison of at least one of the individual compression cycles to at least one of the plurality of evaluation criteria.

11. The method of claim 10, further comprising measuring the victim's electrocardiogram (ECG) and administering a defibrillating shock.

12. The method of claim 10, wherein outputting the matrix of comparisons further comprises arranging the comparisons in rows and columns, wherein one of the rows and columns corresponds to compression cycles and the other of the rows and columns corresponds to the evaluation criteria.

13. The method of claim 10, wherein the evaluation criteria include at least one of compression depth, compression release, compression rate, and inactivity.

14. The method of claim 10, wherein outputting the matrix of comparisons further comprises highlighting portions of the matrix elements corresponding to individual compression cycles failing to satisfy one of the evaluation criteria.

15. The method of claim 10, wherein outputting the matrix of comparisons further comprises highlighting first portions of the matrix elements according to a first color and highlighting second portions of the matrix elements according to a second color, the first highlighted portions corresponding to compression cycles failing to satisfy a test criteria and the second highlighted portions corresponding to compression cycles satisfying a test criteria.

16. The method of claim 10, wherein outputting the matrix of comparisons further comprises plotting graphs of a property of compressions within each of the compression cycles over the time of the CPR session.

17. The method of claim 16, further comprising highlighting portions of the graphs according to a color, the first portions corresponding to portions of the graphs failing to satisfy one of the evaluation criteria.

18. The method of claim 10, wherein outputting the matrix of comparisons comprises outputting the matrix of comparisons to at least one of a display screen and a printer.

19. The method of claim 18, wherein the display screen is coupled to a defibrillator having a power source and electrodes, the power source, electrodes, and compression sensor coupled to a feedback control module programmed to monitor compressions administering to a subject.

* * * * *